(12) United States Patent
't Hooft

(10) Patent No.: US 9,989,510 B2
(45) Date of Patent: Jun. 5, 2018

(54) FLOW CELL AS WELL AS A SYSTEM AND A METHOD FOR ANALYSING A FLUID

(71) Applicant: Rense 't Hooft, Turku (FI)

(72) Inventor: Rense 't Hooft, Turku (FI)

(*) Notice: Subject to any disclaimer, the term of this patent is extended or adjusted under 35 U.S.C. 154(b) by 0 days. days.

(21) Appl. No.: 15/410,896

(22) Filed: Jan. 20, 2017

(65) Prior Publication Data

US 2017/0205386 A1 Jul. 20, 2017

(30) Foreign Application Priority Data

Jan. 20, 2016 (EP) .................................... 16152038

(51) Int. Cl.
| | |
|---|---|
| G01N 23/12 | (2018.01) |
| G01N 33/18 | (2006.01) |
| G01N 23/205 | (2018.01) |
| G01N 23/223 | (2006.01) |
| G01F 1/74 | (2006.01) |

(52) U.S. Cl.
CPC ............ *G01N 33/1893* (2013.01); *G01F 1/74* (2013.01); *G01N 23/12* (2013.01); *G01N 23/2055* (2013.01); *G01N 23/223* (2013.01); *G01N 2223/635* (2013.01); *G01N 2223/637* (2013.01)

(58) Field of Classification Search
CPC ...... G01N 23/12; G01N 23/14; G01N 23/223; G01N 2223/076; G01N 2223/635; G01N 2223/637
See application file for complete search history.

(56) References Cited

U.S. PATENT DOCUMENTS

| | | | |
|---|---|---|---|
| 3,354,308 A | | 11/1967 | Frederick et al. |
| 3,375,802 A | * | 4/1968 | Lazarre .................... B01J 3/004 116/276 |
| 3,409,769 A | * | 11/1968 | McKinney ....... G01N 23/20008 378/143 |
| 3,443,092 A | | 5/1969 | Carr-Brion et al. |
| 4,278,887 A | * | 7/1981 | Lipshutz ............ G01N 21/0303 250/432 R |
| 4,427,892 A | * | 1/1984 | Malcolme-Lawes G01N 23/223 250/458.1 |
| 5,712,891 A | | 1/1998 | Benony et al. |
| 5,893,642 A | * | 4/1999 | Hewitt .................... B01F 5/061 366/142 |

(Continued)

FOREIGN PATENT DOCUMENTS

| | | |
|---|---|---|
| CA | 2038526 A1 | 9/1991 |
| DE | 19911011 A1 | 9/2000 |
| JP | 2010066085 A | 3/2010 |

OTHER PUBLICATIONS

European Patent Office, European Search Report, EP16152038, dated Jun. 22, 2016, The Hague.

*Primary Examiner* — Thomas R Artman
(74) *Attorney, Agent, or Firm* — Berggren LLP

(57) ABSTRACT

The present invention relates to a flow cell that comprises a body defining a cavity, an inlet pipe for the inflow of a fluid to the cavity, an outlet pipe for the outflow of the fluid from the cavity, and an X-ray transparent window for allowing the fluid in the cavity to be irradiated with X-ray radiation. In the flow cell according to the invention the inner surface of the inlet pipe comprises a grooving for imparting rotational flow to the inflowing fluid. The present invention also relates to a system and a method for analysing a fluid.

15 Claims, 4 Drawing Sheets

(56) References Cited

U.S. PATENT DOCUMENTS

| | | |
|---|---|---|
| 7,016,462 B1 | 3/2006 | Keville et al. |
| 8,029,730 B1 * | 10/2011 | Olson ................... G01N 21/05 250/361 C |
| 9,194,848 B2 | 11/2015 | Demarco |
| 2017/0205386 A1 * | 7/2017 | 't Hooft ............. G01N 23/2055 |

* cited by examiner

US 9,989,510 B2

FLOW CELL AS WELL AS A SYSTEM AND A METHOD FOR ANALYSING A FLUID

PRIORITY

This application claims priority of the patent application EP16152038.2 which was filed on Jan. 20, 2016 and the contents of which are incorporated herein by reference.

TECHNICAL FIELD OF THE INVENTION

The present invention relates to a flow cell and a method for analysing a fluid according to the preambles of the appended independent claims. The invention also relates to a system for analysing a fluid, which system comprises a flow cell according to the invention.

BACKGROUND OF THE INVENTION

Various systems utilising X-ray fluorescence (XRF) techniques to analyse fluids, such as effluent waters of a chemical plant, are known in the prior art. FIG. 1 illustrates an example of such a system. The system of FIG. 1 comprises a flow cell 101 (shown as a cross-sectional view) having a body 102 that defines a cavity 103 through which the fluid to be analysed is passed. The fluid flows into the cavity 103 through an inlet pipe 104 and out of the cavity 103 through an outlet pipe 105. The inlet and outlet pipes 104, 105 are attached to opposite ends of the flow cell body 102 in such a manner that the directions of the inflowing and outflowing fluids are essentially the same. The flow cell 101 comprises an X-ray transparent window 106 through which the fluid that flows through the cavity 103 is irradiated with an X-ray source 107. The X-ray transparent window 106 is attached to the side of the flow cell body 102. The irradiated fluid emits fluorescent X-ray radiation that is transmitted through the X-ray transparent window 106 to be detected with an X-ray detector 108. The X-ray detector 108 measures the energy distribution of the fluorescent X-ray radiation in order to obtain information on the composition of the fluid.

A problem associated with the system of FIG. 1 is that, when a fluid flows through the flow cell, particles in the fluid adhere easily on the surface of the X-ray transparent window. As a result of this the compositional analysis of the fluid is difficult or even impossible to carry out as the material adhered to the X-ray transparent window prevents the analysis of the fluid that flows through the cavity.

Another problem associated with the system of FIG. 1 is that, when a fluid flows through the flow cell, heavier particles are easily separated from the lighter particles. This results in incorrect readings at the point of measurement.

OBJECTIVES OF THE INVENTION

It is an objective of the present invention to reduce or even eliminate the prior art problems presented above.

It is an objective of the present invention to provide a flow cell through which a fluid that is to be analysed can be passed. It is also an objective of the invention to provide a flow cell that can be used in an X-ray fluorescence (XRF) system and in an X-ray diffraction (XRD) system. It is a further objective of the invention to provide a flow cell whose window stays clean when a fluid is passed through the flow cell.

It is also an objective of the present invention to provide a flow cell in which heavier particles of a fluid are not easily separated from the lighter ones.

It is also an objective of the invention to provide a system and a method that enables the analysis of fluids, such as effluent waters of a chemical plant, reliably and accurately. It is a further objective of the invention to provide a system and a method that enables real-time analysis of fluids.

In order to realise the above-mentioned objectives, the flow cell and the method according to the invention are characterised by what is presented in the appended independent claims. Advantageous embodiments of the invention are described in the dependent claims.

DESCRIPTION OF THE INVENTION

A typical flow cell according to the invention comprises a body that defines a cavity, an inlet pipe for the inflow of a fluid to the cavity, an outlet pipe for the outflow of the fluid from the cavity, and an X-ray transparent window for allowing the fluid in the cavity to be irradiated with X-ray radiation. In a typical flow cell according to the invention the inner surface of the inlet pipe comprises a grooving for imparting rotational flow to the inflowing fluid.

In the flow cell according to the invention a fluid, such as effluent waters of a chemical plant, is led into the cavity through the inlet pipe and out of the cavity through the outlet pipe. The inlet and outlet pipes are attached to the body of the flow cell. The inlet pipe is preferably arranged to direct the inflowing fluid upwards into the cavity. The inlet pipe may be arranged to direct the inflowing fluid towards the wall of the cavity or the X-ray transparent window. The fluid is preferably directed into the cavity in such a manner that the fluid flows essentially along the wall of the cavity. Preferably, the fluid is guided by the wall of the cavity towards the outlet pipe so that the fluid can easily flow out of the cavity.

The inlet and outlet pipes are attached at their first ends to the body of the flow cell. The inlet and outlet pipes are preferably attached to a lower part of the flow cell body. The cavity has preferably an essentially rounded shape. The volume of the cavity can be, for example, in the range of 0.05 to 0.5 liters. The inner diameter of the inlet and outlet pipes can be, for example, in the range of 15 to 28 mm, and the length of the inlet and outlet pipes can be, for example, in the range of 25 to 50 cm. The body of the flow cell as well as the inlet and outlet pipes are preferably made of a metal such as brass or stainless steel.

The X-ray transparent window is attached to an opening in the flow cell body. The X-ray transparent window is preferably attached to the upper part of the flow cell body. The X-ray transparent window can be made of, for example, coated beryllium or diamond. The length of the window can be, for example, in the range of 2 to 4 cm, and the width of the window can be, for example, in the range of 1 to 2 cm.

The X-ray transparent window enables the fluid flowing through the cavity to be irradiated with an X-ray source and the fluorescent X-ray radiation emitted by the irradiated fluid to be detected with an X-ray detector. The purpose of irradiating the fluid is to release electrons from the innermost shells of atoms in the fluid. The resultant vacancies are then filled by electrons from the outer shells of the atoms. During these transitions, fluorescent X-ray radiation is generated that is characteristic for each element. This fluorescent X-ray radiation, which is detected by the X-ray detector, thus provides information on the composition of the fluid, and therefore enables the detection, for example, of any unwanted elements in the fluid.

The X-ray transparent window enables the fluid flowing through the cavity to be irradiated with an X-ray source and the X-ray radiation diffracted by the fluid to be detected with an X-ray detector. When the fluid is irradiated with X-ray radiation, the crystalline atoms in the fluid cause a beam of incident X-rays to diffract into many specific directions. By measuring the angles and intensities of these diffracted beams, a three-dimensional picture of the density of electrons within the crystal can be produced. From this electron density, the mean positions of the atoms in the crystal can be determined as well as their chemical bonds.

In the flow cell according to the invention the inner surface of the inlet pipe is provided with a grooving that imparts rotational flow to the fluid that flows into the cavity. In the cavity, a third dimension is added to the flow, so that the flow becomes turbulent. It has been found that due to this turbulent flow the surface of the X-ray transparent window of the flow cell stays clean. In other words, the rotational flow of the inflowing fluid prevents particles of the fluid from adhering to the surface of the X-ray transparent window. The turbulence of the flow inside the cavity of the flow cell also ensures the representativeness of the sample at the measuring point in relation to the total flow because heavier particles of the fluid are not easily separated from the lighter ones.

The grooving in the inner surface of the inlet pipe preferably extends from the first end of the inlet pipe towards its second end. The grooving may extend along the whole length of the inlet pipe. Preferably, at least 25 cm of the length of the inlet pipe is grooved. The grooving can be made on the inner surface of the inlet pipe by milling or by hammering.

The flow cell according to the invention can be used in an X-ray fluorescence (XRF) system that is configured to detect elements in flowing fluids. The flow cell according to the invention can also be used in an X-ray diffraction (XRD) system that is configured to detect the atomic and molecular structure of the fluid. The flow cell is advantageously used in applications where the fluid needs to be analysed in real-time and where the composition of the fluid can change rapidly.

According to an embodiment of the invention the grooving comprises helical grooves having a helix angle in the range of 20 to 45 degrees. The helix angle of the helical grooves affects the flow behavior of the fluid, i.e. what kind of rotational flow is imparted by the grooving to the inflowing fluid. The optimal value of the helix angle can vary, and it may depend, for example, on the composition of the fluid and its flow rate.

According to an embodiment of the invention the depth of the helical grooves is in the range of 0.5 to 2.0 mm. The optimal value of the depth of the helical grooves can vary, and it may depend, for example, on the size of the particles in the fluid.

According to an embodiment of the invention the inlet pipe is arranged to direct the inflowing fluid towards the X-ray transparent window. Directing the inflowing fluid towards the X-ray transparent window makes it more difficult for the particles in the fluid to adhere to the surface of the window, and thus the window stays clean for a longer time.

According to an embodiment of the invention the inlet pipe is arranged to direct the inflowing fluid into the cavity in such a manner that the fluid flows essentially along the wall of the cavity. An advantage of arranging the fluid to flow essentially along the wall of the cavity is that the particles in the fluid cannot easily adhere to the surface of the X-ray transparent window, and thus the window stays clean for a longer time.

According to an embodiment of the invention the angle between the directions of the inflowing fluid and the outflowing fluid is in the range of 45 to 180 degrees. Because of the difference between the directions of the inflowing and outflowing fluids and the interaction of the fluid with the wall of the cavity, the turbulence of the fluid that flows inside the cavity can be increased. This makes it more difficult for the particles in the fluid to adhere to the surface of the X-ray transparent window. This also improves the representativeness of the sample fluid at the measuring point.

According to an embodiment of the invention the inlet pipe and the outlet pipe are attached to the same side of the body. The inlet and outlet pipes are preferably arranged close to the opposite end walls of the cavity and directed in such a manner that the angle between the directions of the inflowing fluid and the outflowing fluid is essentially 180 degrees. This means that the inflowing and outflowing fluids flow in essentially opposite directions. With this arrangement, the fluid can be arranged to flow essentially along the wall of the cavity.

According to an embodiment of the invention the X-ray transparent window is attached to the side of the body opposite to the inlet and outlet pipes.

According to an embodiment of the invention the cavity has essentially the shape of a spheroid. The spheroidal cavity has been found to prevent effectively the adherence of particles in the fluid on the surface of the X-ray transparent window.

According to an embodiment of the invention the cavity wall between the inlet pipe and the outlet pipe is convex shaped. Because of the convexity, any sediments in the fluid cannot easily accumulate on the bottom of the cavity.

According to an embodiment of the invention the X-ray transparent window is made of diamond. The diamond window can be manufactured using high-pressure high-temperature (HPHT) or chemical vapour deposition (CVD) crystal formation methods.

The present invention also relates to a system for analysing a fluid. A typical system according to the invention comprises a flow cell according to the invention for receiving the fluid, an X-ray source for irradiating the fluid in the flow cell, and an X-ray detector for detecting the X-ray radiation emitted or diffracted by the fluid. In the system according to the invention the X-ray source and the X-ray detector are located outside the flow cell. The fluid inside the cavity of the flow cell is irradiated through the X-ray transparent window using the X-ray source. The X-ray source comprises an X-ray tube, which is a vacuum tube that produces X-rays. The fluorescent X-ray radiation or the diffracted X-ray radiation that passes through the X-ray transparent window is detected by using the X-ray detector. The X-ray detector is a device used to measure the flux, spatial distribution, spectrum or other properties of X-rays.

According to an embodiment of the invention the X-ray source and the X-ray detector are oriented in such a manner that the fluid flowing at a depth of 0.5 to 4.0 mm measured from the inner surface of the X-ray transparent window can be analysed.

According to an embodiment of the invention the system comprises a pump coupled to the inlet pipe for pumping the fluid through the cavity. The pump is needed in situations where the natural flow of the fluid to be analysed is not sufficient. The pump can be used to provide a constant or a variable flow rate. The flow rate of the fluid can be changed, for example, based on the viscosity of the fluid.

The present invention further relates to a method for analysing a fluid. A typical method according to the invention comprises passing the fluid through a cavity of a flow cell, irradiating the fluid in the cavity with an X-ray source, and detecting the X-ray radiation emitted or diffracted by the fluid with an X-ray detector. A typical method according to the invention further comprises imparting rotational flow to the inflowing fluid with a grooving on the inner surface of an inlet pipe of the flow cell. In the cavity, the rotational flow is transformed with the help of the rounded shape of the cavity walls of the flow cell into a turbulent flow.

The system and method according to the invention enable to analyse fluids, such as effluent waters of a chemical plant, prompt, reliably and accurately. The system and method according to the invention enable to analyse fluids in real-time.

The exemplary embodiments of the invention presented in this text are not interpreted to pose limitations to the applicability of the appended claims. The verb "to comprise" is used in this text as an open limitation that does not exclude the existence of also unrecited features. The features recited in the dependent claims are mutually freely combinable unless otherwise explicitly stated.

The exemplary embodiments presented in this text and their advantages relate by applicable parts to the flow cell as well as the system and method according to the invention, even though this is not always separately mentioned.

DETAILED DESCRIPTION OF THE DRAWINGS

Figure 1:
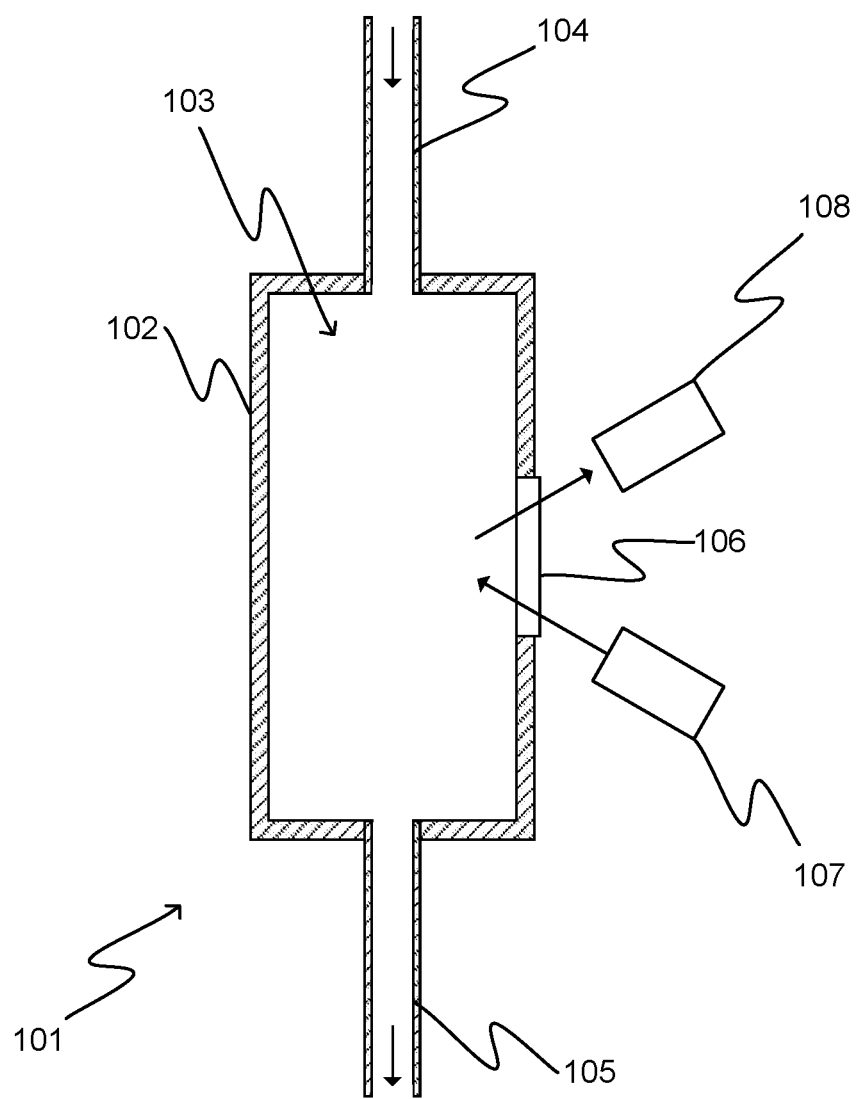
FIG. 1 illustrates an example of a known system for analysing a fluid.

FIG. 1 has already been described with reference to the background of the invention. Embodiments of the invention will now be described with reference to FIGS. 2-4. The same reference signs are used for the same or like components in different embodiments.

Figure 2:
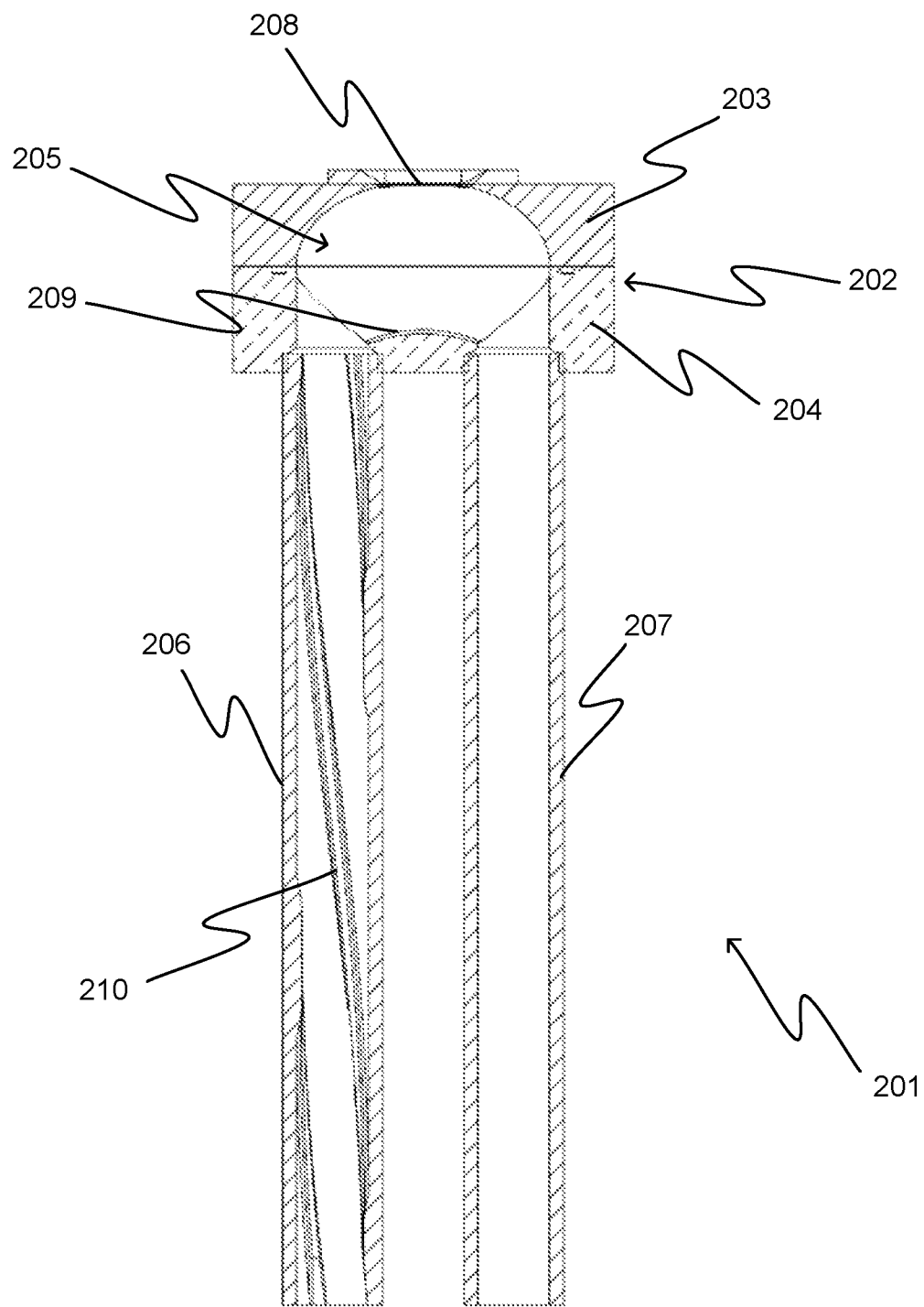
FIG. 2 illustrates a flow cell according to a first embodiment of the invention.

FIG. 2 illustrates a cross-sectional view of a flow cell according to a first embodiment of the invention. The flow cell 201 comprises a body 202, which comprises an upper part 203 and a lower part 204 coupled together. The body 202 defines a spheroidal cavity 205 through which the fluid to be analysed is passed. The fluid is led into the cavity 205 through an inlet pipe 206 and out of the cavity 205 through an outlet pipe 207. The inlet and outlet pipes 206, 207 are attached at their ends to the lower part 204 of the flow cell body 202 in such a manner that the angle between the directions of the inflow and the outflow of the fluid is approximately 180 degrees. The flow cell 201 also comprises an X-ray transparent window 208, which is attached to an opening in the upper part 203 of the flow cell body 202, opposite to the inlet and outlet pipes 206, 207. The X-ray transparent window 208 enables the fluid flowing through the cavity 205 to be irradiated with X-ray radiation and the fluorescent X-ray radiation emitted by the irradiated fluid to be detected. In the flow cell 201 according to the first embodiment of the invention, the inlet pipe 206 directs the inflowing fluid upwards into the cavity 205 in such a manner that the fluid flows along the wall of the cavity 205 towards the outlet pipe 207 so that the fluid can easily flow out of the cavity 205. The convex-shaped bottom wall 209 of the cavity 205 between the inlet and outlet pipes 206, 207 decreases accumulation of the sediments in the fluid on the bottom of the cavity 205. An inner surface of the inlet pipe 206 is provided with a grooving 210 for imparting rotational flow to the inflowing fluid. The grooving 210 comprises helical grooves having a helix angle of approximately 20 degrees and extending along the whole length of the inlet pipe 206. In the cavity 205, a third dimension is added to the rotational inflow by the shape of the cavity walls, so that the flow becomes turbulent. Turbulence of the inflowing fluid prevents adherence of the particles in the fluid on the surface of the X-ray transparent window 208. And this also improves the representativeness of the sample fluid at the point of measurement.

Figures 3A, 3B:
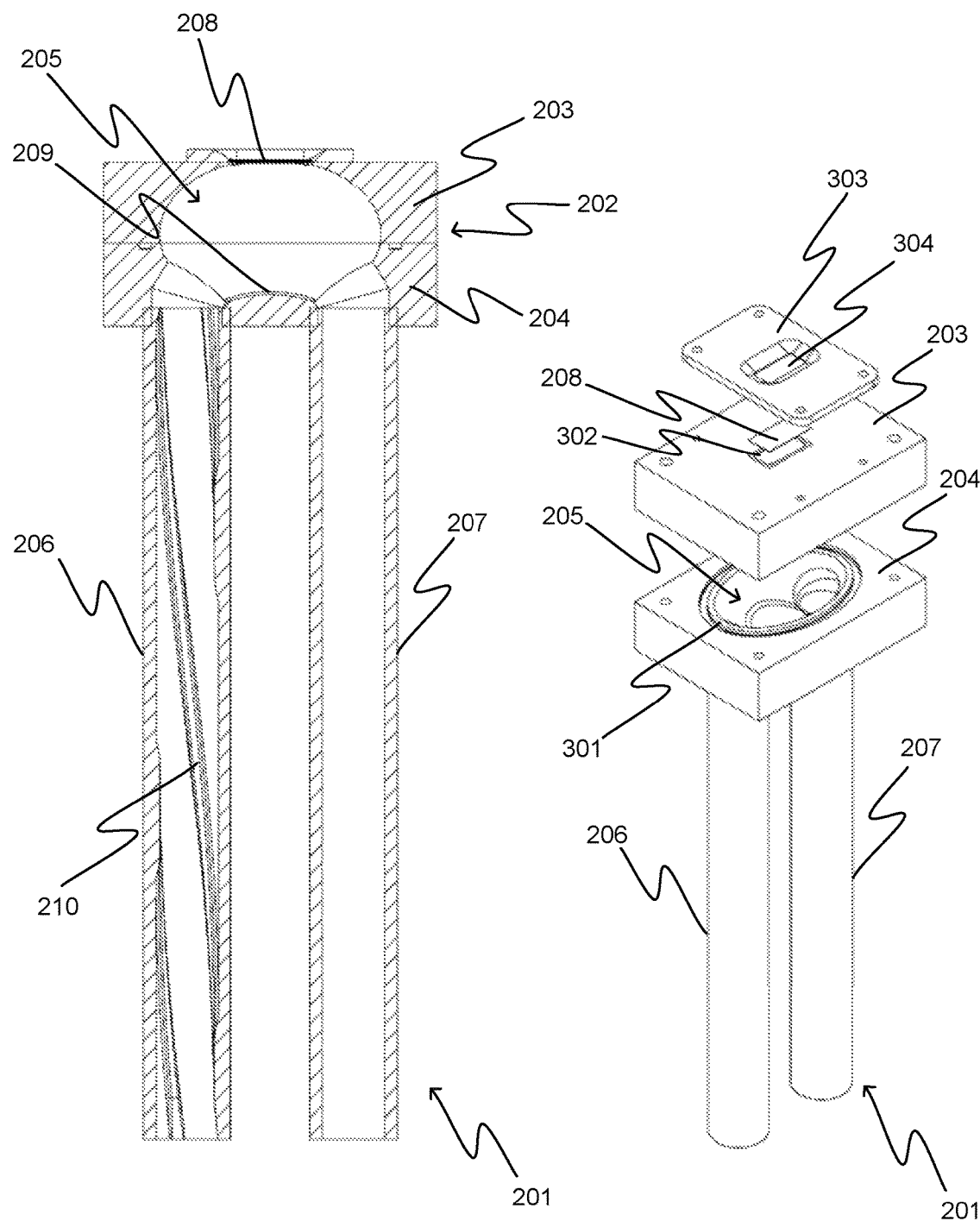
FIGS. 3a-3b illustrate a flow cell according to a second embodiment of the invention.

FIG. 3a illustrates a cross-sectional view of a flow cell according to a second embodiment of the invention. The difference between the flow cells of FIGS. 2 and 3a is that in the flow cell of FIG. 3a the inlet pipe 206 is arranged to direct the inflowing fluid towards the X-ray transparent window 208. This makes it more difficult for the particles in the fluid to adhere to the surface of the window 208, and thus the window 208 stays clean for a longer time.

FIG. 3b illustrates the flow cell of FIG. 3a as an exploded view. The upper part 203 and the lower part 204 of the flow cell body 202 can be fastened together with screws. For sealing purpose, a sealing ring 301 is arranged between the upper and lower parts 203, 204 of the body 202. The upper part 203 of the flow cell body 202 has the opening 302 where the X-ray transparent window 208 can be placed. The X-ray transparent window 208 is held in place with a plate 303, which can be fastened to the outer surface of the upper part 203 of the body 202 with screws. The plate 303 has an opening 304 for the X-ray transparent window 208 through which the fluid flowing in the cavity 205 is to be irradiated.

Figure 4:
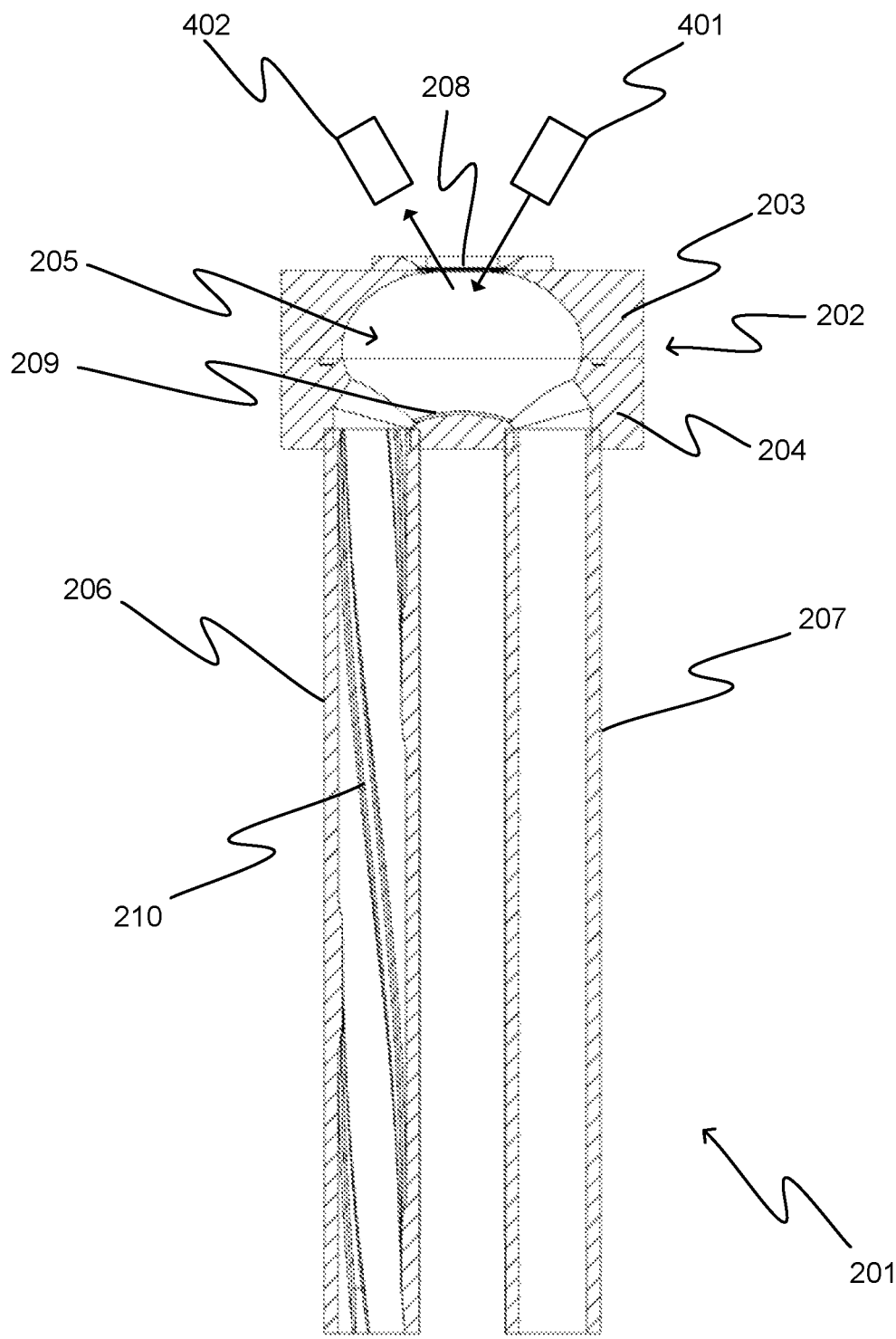
FIG. 4 illustrates a system for analysing a fluid according to an embodiment of the invention.

FIG. 4 illustrates a cross-sectional view of a system for analysing a fluid according to an embodiment of the invention. The system comprises the flow cell 201 as presented in FIG. 3a, as well as an X-ray source 401 and an X-ray detector 402, which are located outside the flow cell 201. The X-ray source 401 is used for irradiating the fluid inside the cavity 205 of the flow cell 201 through the X-ray transparent window 208. The X-ray source 401 comprises an X-ray tube, which is a vacuum tube that produces X-rays. The purpose of irradiating the fluid is to release electrons from the innermost shells of atoms in the fluid. The resultant vacancies are then filled by electrons from the outer shells of the atoms. During these transactions, fluorescent X-ray radiation is generated that is characteristic for each element. The fluorescent X-ray radiation that passes through the X-ray transparent window 208 is detected using the X-ray detector 402. The X-ray detector 402 measures the energy distribution of the fluorescent X-ray radiation in order to obtain information on the composition of the fluid.

Only advantageous exemplary embodiments of the invention are described in the figures. It is clear to a person skilled in the art that the invention is not restricted only to the examples presented above, but the invention may vary within the limits of the claims presented hereafter. Some possible embodiments of the invention are described in the dependent claims, and they are not to be considered to restrict the scope of protection of the invention as such.

The invention claimed is:

1. A flow cell, comprising:
a body that defines a cavity,
an inlet pipe for the inflow of a fluid to the cavity,
an outlet pipe for the outflow of the fluid from the cavity, and
an X-ray transparent window for allowing the fluid in the cavity to be irradiated with X-ray radiation,
wherein the inner surface of the inlet pipe comprises a grooving for imparting rotational flow to the inflowing fluid.

2. The flow cell according to claim 1, wherein the grooving comprises helical grooves having a helix angle in the range of 20 to 45 degrees.

3. The flow cell according to claim 2, wherein the depth of the helical grooves is in the range of 0.5 to 2.0 mm.

4. The flow cell according to claim 1, wherein the inlet pipe is arranged to direct the inflowing fluid towards the X-ray transparent window.

5. The flow cell according to claim 1, wherein the inlet pipe is arranged to direct the inflowing fluid into the cavity in such a manner that the fluid flows essentially along the wall of the cavity.

6. The flow cell according to claim 1, wherein the angle between the directions of the inflowing fluid and the outflowing fluid is in the range of 45 to 180 degrees.

7. The flow cell according to claim 1, wherein the inlet pipe and the outlet pipe are attached to the same side of the body.

8. The flow cell according to claim 7, wherein the X-ray transparent window is attached to the side of the body opposite to the inlet and outlet pipes.

9. The flow cell according to claim 1, wherein the cavity has essentially the shape of a spheroid.

10. The flow cell according to claim 1, wherein the cavity wall between the inlet pipe and the outlet pipe is convex shaped.

11. The flow cell according to claim 1, wherein the X-ray transparent window is made of diamond.

12. A system for analysing a fluid, comprising:
a flow cell for receiving the fluid,
an X-ray source for irradiating the fluid in the flow cell, and
an X-ray detector for detecting the X-ray radiation emitted or diffracted by the fluid,
wherein the flow cell is according to claim 1.

13. The system according to claim 12, wherein the X-ray source and the X-ray detector are oriented in such a manner that the fluid flowing at a depth of 0.5 to 4.0 mm measured from the inner surface of the X-ray transparent window can be analysed.

14. The system according to claim 12, wherein the system comprises a pump coupled to the inlet pipe for pumping the fluid through the cavity.

15. A method for analysing a fluid, comprising:
passing the fluid through a cavity of a flow cell,
irradiating the fluid in the cavity with an X-ray source,
detecting the X-ray radiation emitted or diffracted by the fluid with an X-ray detector, and
imparting rotational flow to the inflowing fluid with a grooving on the inner surface of an inlet pipe of the flow cell.

* * * * *